(12) United States Patent
Keating et al.

(10) Patent No.: US 11,633,198 B2
(45) Date of Patent: Apr. 25, 2023

(54) CATHETER PROXIMAL JOINT

(71) Applicant: Neuravi Limited, Galway (IE)

(72) Inventors: Karl Keating, Galway (IE); Ronald Kelly, Galway (IE); David Vale, Galway (IE)

(73) Assignee: Neuravi Limited, Galway (IE)

( * ) Notice: Subject to any disclaimer, the term of this patent is extended or adjusted under 35 U.S.C. 154(b) by 415 days.

(21) Appl. No.: 16/809,941

(22) Filed: Mar. 5, 2020

(65) Prior Publication Data

US 2021/0275198 A1 Sep. 9, 2021

(51) Int. Cl.
  *A61B 17/22* (2006.01)
  *A61B 17/00* (2006.01)
  *A61M 25/00* (2006.01)

(52) U.S. Cl.
  CPC ...... *A61B 17/22* (2013.01); *A61B 2017/0084* (2013.01); *A61B 2017/00898* (2013.01); *A61B 2017/22049* (2013.01); *A61B 2017/22079* (2013.01); *A61M 25/0068* (2013.01)

(58) Field of Classification Search
  CPC ............ A61B 17/22; A61B 2017/0084; A61B 2017/00898; A61B 2017/22049
  See application file for complete search history.

(56) References Cited

U.S. PATENT DOCUMENTS

| | | |
|---|---|---|
| 4,243,040 A | 1/1981 | Beecher |
| 4,324,262 A | 4/1982 | Hall |
| 4,351,342 A | 9/1982 | Wiita et al. |
| 4,575,371 A | 3/1986 | Nordqvist et al. |
| 4,592,356 A | 6/1986 | Gutierrez |
| 4,719,924 A | 1/1988 | Crittenden et al. |
| 4,738,666 A | 4/1988 | Fuqua |

(Continued)

FOREIGN PATENT DOCUMENTS

| | | |
|---|---|---|
| CN | 1658920 A | 8/2005 |
| CN | 1972728 A | 5/2007 |

(Continued)

OTHER PUBLICATIONS

US 6,348,062 B1, 02/2002, Hopkins (withdrawn)

(Continued)

*Primary Examiner* — Alexander J Orkin
(74) *Attorney, Agent, or Firm* — Troutman Pepper Hamilton Sanders LLP

(57) ABSTRACT

An aspiration clot retrieval catheter to have profiled guidewire for deliverability that transitions at a proximal joint to a distal tubular section with a lumen for directing aspiration and facilitating the smooth passage of other products in performing mechanical thrombectomy procedures. The joint can have a low-profile proximal strut formed integrally with the distal tubular section and configured to interlock with a distal portion of the guidewire so that there is a smooth transition of stiffness between the guidewire and the tubular portion of the catheter to improve trackability and decrease the likelihood of kinking. The distal tubular section of the proximal joint can also have features to tailor flexibility. The tubular section can be configured to push radially outward to form a seal with an outer catheter to optimize aspiration transmission to the distal mouth of the aspiration clot retrieval catheter.

20 Claims, 5 Drawing Sheets

(56) References Cited

U.S. PATENT DOCUMENTS

| | | |
|---|---|---|
| 4,767,404 A | 8/1988 | Renton |
| 4,793,348 A | 12/1988 | Palmaz |
| 4,873,978 A | 10/1989 | Ginsburg |
| 5,011,488 A | 4/1991 | Ginsburg |
| 5,092,839 A | 3/1992 | Kipperman |
| 5,102,415 A | 4/1992 | Guenther et al. |
| 5,122,136 A | 6/1992 | Guglielmi et al. |
| 5,123,840 A | 6/1992 | Nates |
| 5,171,233 A | 12/1992 | Amplatz |
| 5,234,437 A | 8/1993 | Sepetka |
| 5,256,144 A | 10/1993 | Kraus et al. |
| 5,261,916 A * | 11/1993 | Engelson ......... A61B 17/12022 606/1 |
| 5,372,124 A | 12/1994 | Takayama et al. |
| 5,385,562 A | 1/1995 | Adams |
| 5,387,219 A | 2/1995 | Rappe |
| 5,387,226 A | 2/1995 | Miraki |
| 5,396,902 A | 3/1995 | Brennen et al. |
| 5,449,372 A | 9/1995 | Schmaltz |
| 5,520,651 A | 5/1996 | Sutcu |
| 5,538,512 A | 7/1996 | Zenzon et al. |
| 5,549,626 A | 8/1996 | Miller et al. |
| 5,558,652 A | 9/1996 | Henke |
| 5,601,600 A * | 2/1997 | Ton .................. A61B 17/12022 606/198 |
| 5,609,627 A | 3/1997 | Goicoechea et al. |
| 5,624,461 A | 4/1997 | Mariant |
| 5,639,277 A | 6/1997 | Mariant |
| 5,645,558 A | 7/1997 | Horton |
| 5,658,296 A | 8/1997 | Bates |
| 5,662,671 A | 9/1997 | Barbut |
| 5,695,519 A | 12/1997 | Summer et al. |
| 5,709,704 A | 1/1998 | Nott et al. |
| 5,713,853 A | 2/1998 | Clark |
| 5,728,078 A | 3/1998 | Powers, Jr. |
| 5,769,871 A | 6/1998 | Mers Kelly |
| 5,779,716 A | 7/1998 | Cano |
| 5,810,874 A | 9/1998 | Lefebvre |
| 5,814,064 A | 9/1998 | Danniel et al. |
| 5,827,304 A | 10/1998 | Hart |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,725 A | 6/1999 | Boury |
| 5,935,139 A | 8/1999 | Bates |
| 5,938,645 A | 8/1999 | Gordon |
| 5,947,995 A | 9/1999 | Samuels |
| 5,968,057 A | 10/1999 | Taheri |
| 5,971,938 A | 10/1999 | Hart et al. |
| 5,997,939 A | 12/1999 | Moechnig et al. |
| 6,022,343 A | 2/2000 | Johnson et al. |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,102,932 A | 8/2000 | Kurz |
| 6,106,548 A | 8/2000 | Roubin et al. |
| 6,129,739 A | 10/2000 | Khosravi |
| 6,146,396 A | 11/2000 | Kónya et al. |
| 6,146,404 A | 11/2000 | Kim |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,238,412 B1 | 5/2001 | Dubrul |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,306,163 B1 | 10/2001 | Fitz |
| 6,309,379 B1 | 10/2001 | Willard |
| 6,312,444 B1 | 11/2001 | Barbut |
| 6,315,778 B1 | 11/2001 | Gambale et al. |
| 6,325,819 B1 | 12/2001 | Pavcnik et al. |
| 6,334,864 B1 | 1/2002 | Amplatz et al. |
| 6,336,934 B1 | 1/2002 | Gilson et al. |
| 6,348,056 B1 | 2/2002 | Bates |
| 6,350,271 B1 | 2/2002 | Kurz et al. |
| 6,361,545 B1 | 3/2002 | Macoviak |
| 6,371,963 B1 | 4/2002 | Nishtala et al. |
| 6,375,668 B1 | 4/2002 | Gifford et al. |
| 6,382,742 B1 | 5/2002 | Hasselbusch et al. |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,409,683 B1 | 6/2002 | Fonseca et al. |
| 6,416,541 B2 | 7/2002 | Denardo |
| 6,425,909 B1 | 7/2002 | Dieck et al. |
| 6,432,122 B1 | 8/2002 | Gilson et al. |
| 6,436,112 B2 | 8/2002 | Wensel |
| 6,458,139 B1 | 10/2002 | Palmer |
| 6,346,116 B1 | 11/2002 | Brooks et al. |
| 6,485,497 B2 | 11/2002 | Wensel |
| 6,485,501 B1 | 11/2002 | Green |
| 6,485,502 B2 | 11/2002 | Don Michael |
| 6,511,492 B1 | 1/2003 | Rosenbluth |
| 6,517,551 B1 | 2/2003 | Driskill |
| 6,520,934 B1 | 2/2003 | Lee et al. |
| 6,520,951 B1 | 2/2003 | Carrillo, Jr. |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,616 B1 | 7/2003 | Stack |
| 6,602,271 B2 | 8/2003 | Adams |
| 6,602,272 B2 | 8/2003 | Boylan et al. |
| 6,605,102 B1 | 8/2003 | Mazzocchi et al. |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,652,555 B1 | 11/2003 | VanTassel et al. |
| 6,656,218 B1 | 12/2003 | Denardo et al. |
| 6,660,021 B1 | 12/2003 | Palmer et al. |
| 6,663,650 B2 | 12/2003 | Sepetka |
| 6,673,089 B1 | 1/2004 | Yassour et al. |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,702,782 B2 | 3/2004 | Miller |
| 6,712,834 B2 | 3/2004 | Yassour et al. |
| 6,726,701 B2 | 4/2004 | Gilson et al. |
| 6,730,104 B1 | 5/2004 | Sepetka |
| 6,726,703 B2 | 8/2004 | Broome et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,953,472 B2 | 10/2005 | Palmer et al. |
| 6,989,019 B2 | 1/2006 | Mazzocchi |
| 6,989,021 B2 | 1/2006 | Bosma et al. |

(56) References Cited

U.S. PATENT DOCUMENTS

| | | |
|---|---|---|
| 6,994,718 B2 | 2/2006 | Groothuis et al. |
| 6,997,939 B2 | 2/2006 | Linder |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,058,456 B2 | 6/2006 | Pierce |
| 7,063,707 B2 | 6/2006 | Bose |
| 7,153,320 B2 | 12/2006 | Euteneuer et al. |
| 7,175,655 B1 | 2/2007 | Malaei |
| 7,179,273 B1 | 2/2007 | Palmer et al. |
| 7,220,269 B1 | 5/2007 | Ansel |
| 7,220,271 B2 | 5/2007 | Clubb |
| 7,226,464 B2 | 6/2007 | Garner et al. |
| 7,229,472 B2 | 6/2007 | DePalma et al. |
| 7,232,462 B2 | 6/2007 | Schaeffer |
| 7,288,112 B2 | 10/2007 | Denardo et al. |
| 7,306,618 B2 | 12/2007 | Demond |
| 7,316,692 B2 | 1/2008 | Huffmaster |
| 7,323,001 B2 | 1/2008 | Cubb |
| 7,331,976 B2 | 2/2008 | McGuckin, Jr. et al. |
| 7,344,550 B2 | 3/2008 | Carrison et al. |
| 7,399,308 B2 | 7/2008 | Borillo et al. |
| 7,410,491 B2 | 8/2008 | Hopkins |
| 7,452,496 B2 | 11/2008 | Brady et al. |
| 7,491,215 B2 | 2/2009 | Vale et al. |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik et al. |
| 7,594,926 B2 | 9/2009 | Linder |
| 7,604,649 B2 | 10/2009 | McGuckin et al. |
| 7,618,434 B2 | 11/2009 | Santra et al. |
| 7,662,165 B2 | 2/2010 | Gilson et al. |
| 7,670,356 B2 | 3/2010 | Mazzocchi |
| 7,691,121 B2 | 4/2010 | Rosenbluth |
| 7,691,124 B2 | 4/2010 | Balgobin |
| 7,708,770 B2 | 5/2010 | Linder |
| 7,736,385 B2 | 6/2010 | Agnew |
| 7,766,934 B2 | 8/2010 | Pal |
| 7,771,452 B2 | 8/2010 | Pal |
| 7,780,694 B2 | 8/2010 | Palmer |
| 7,780,696 B2 | 8/2010 | Daniel et al. |
| 7,819,893 B2 | 10/2010 | Brady et al. |
| 7,828,815 B2 | 11/2010 | Mazzocchi |
| 7,846,176 B2 | 11/2010 | Mazzocchi |
| 7,846,175 B2 | 12/2010 | Bonnette et al. |
| 7,850,708 B2 | 12/2010 | Pal |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,349 B2 | 4/2011 | Brady et al. |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,066,757 B2 | 11/2011 | Ferrera et al. |
| 8,070,791 B2 | 12/2011 | Ferrera et al. |
| 8,088,140 B2 | 1/2012 | Ferrera et al. |
| 8,100,935 B2 | 1/2012 | Rosenbluth et al. |
| 8,109,941 B2 | 2/2012 | Richardson |
| 8,118,829 B2 | 2/2012 | Garrison et al. |
| 8,123,769 B2 | 2/2012 | Osborne |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,357,178 B2 | 1/2013 | Grandfield et al. |
| 8,357,179 B2 | 1/2013 | Grandfield et al. |
| 8,357,893 B2 | 1/2013 | Xu et al. |
| 8,361,095 B2 | 1/2013 | Osborne |
| 8,366,663 B2 | 2/2013 | Fiorella et al. |
| 8,372,133 B2 | 2/2013 | Douk et al. |
| 8,409,215 B2 | 4/2013 | Sepetka et al. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,529,596 B2 | 9/2013 | Grandfield et al. |
| 8,574,262 B2 | 11/2013 | Ferrera et al. |
| 8,579,915 B2 | 11/2013 | French et al. |
| 8,585,643 B2 | 11/2013 | Vo et al. |
| 8,585,713 B2 | 11/2013 | Ferrera et al. |
| 8,608,761 B2 | 12/2013 | Osbourne et al. |
| 8,679,142 B2 | 3/2014 | Slee et al. |
| 8,696,622 B2 | 4/2014 | Fiorella et al. |
| 8,702,652 B2 | 4/2014 | Fiorella et al. |
| 8,702,724 B2 | 4/2014 | Olsen et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,900,265 B1 | 12/2014 | Ulm, III |
| 8,939,991 B2 | 1/2015 | Krolick et al. |
| 8,945,143 B2 | 2/2015 | Ferrera et al. |
| 8,945,172 B2 | 2/2015 | Ferrera et al. |
| 8,968,330 B2 | 3/2015 | Rosenbluth et al. |
| 9,039,749 B2 | 5/2015 | Shrivastava et al. |
| 9,072,537 B2 | 7/2015 | Grandfield et al. |
| 9,113,936 B2 | 8/2015 | Palmer et al. |
| 9,119,656 B2 | 9/2015 | Bose et al. |
| 9,138,307 B2 | 9/2015 | Valaie |
| 9,149,609 B2 | 10/2015 | Ansel et al. |
| 9,155,552 B2 | 10/2015 | Ulm, III |
| 9,161,766 B2 | 10/2015 | Slee et al. |
| 9,173,668 B2 | 11/2015 | Ulm, III |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,635 B2 | 5/2017 | Vale et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |

(56) References Cited

U.S. PATENT DOCUMENTS

| | | |
|---|---|---|
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 10,028,759 B2 | 7/2018 | Wallace et al. |
| 10,149,692 B2 | 12/2018 | Turjman et al. |
| 10,265,086 B2 | 4/2019 | Vale |
| 10,716,915 B2 | 7/2020 | Ogle et al. |
| 10,610,668 B2 | 8/2020 | Burkholz et al. |
| 2001/0001315 A1 | 5/2001 | Bates |
| 2001/0011182 A1 | 8/2001 | Dubrul et al. |
| 2001/0016755 A1 | 8/2001 | Addis |
| 2001/0041899 A1 | 11/2001 | Foster |
| 2001/0044598 A1 | 11/2001 | Parodi |
| 2001/0044634 A1 | 11/2001 | Don Michael et al. |
| 2001/0051810 A1 | 12/2001 | Dubrul |
| 2002/0002383 A1 | 1/2002 | Sepetka et al. |
| 2002/0016609 A1 | 2/2002 | Wensel |
| 2002/0022859 A1 | 2/2002 | Hogendijk |
| 2002/0026211 A1 | 2/2002 | Khosravi |
| 2002/0049468 A1 | 4/2002 | Streeter |
| 2002/0052620 A1 | 5/2002 | Barvut |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0143362 A1 | 10/2002 | Macoviak et al. |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0177800 A1 | 11/2002 | Bagaoisan et al. |
| 2002/0188276 A1 | 12/2002 | Evans |
| 2003/0004536 A1 | 1/2003 | Boylan et al. |
| 2003/0004538 A1 | 1/2003 | Secrest |
| 2003/0004542 A1 | 1/2003 | Wensel |
| 2003/0009146 A1 | 1/2003 | Muni |
| 2003/0009191 A1 | 1/2003 | Wensel |
| 2003/0023204 A1 | 1/2003 | Vo et al. |
| 2003/0040769 A1 | 2/2003 | Kelley et al. |
| 2003/0040772 A1 | 2/2003 | Hyodoh et al. |
| 2003/0050663 A1 | 3/2003 | Khachin |
| 2003/0105484 A1 | 6/2003 | Boyle et al. |
| 2003/0125798 A1 | 7/2003 | Martin |
| 2003/0130682 A1 | 7/2003 | Broome et al. |
| 2003/0144687 A1 | 7/2003 | Brady et al. |
| 2003/0153940 A1 | 8/2003 | Nohilly et al. |
| 2003/0153943 A1 | 8/2003 | Michael et al. |
| 2003/0153944 A1 | 8/2003 | Phung |
| 2003/0163064 A1 | 8/2003 | Vrba |
| 2003/0163158 A1 | 8/2003 | Wlite |
| 2003/0171769 A1 | 9/2003 | Barbul |
| 2003/0176884 A1 | 9/2003 | Berrada et al. |
| 2003/0187495 A1* | 10/2003 | Cully .............. A61B 17/12109 623/1.34 |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0212430 A1 | 11/2003 | Bose |
| 2003/0216611 A1 | 11/2003 | Vu |
| 2003/0236533 A1 | 12/2003 | Wilson |
| 2004/0010280 A1 | 1/2004 | Adams et al. |
| 2004/0010282 A1 | 1/2004 | Kusleika |
| 2004/0014002 A1 | 1/2004 | Lundgren |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0093065 A1 | 5/2004 | Yachia et al. |
| 2004/0133231 A1 | 7/2004 | Maitland |
| 2004/0138692 A1 | 7/2004 | Phung |
| 2004/0153049 A1 | 8/2004 | Hewitt et al. |
| 2004/0153118 A1 | 8/2004 | Clubb |
| 2004/0193107 A1 | 9/2004 | Pierpont et al. |
| 2004/0199202 A1 | 10/2004 | Dubrul et al. |
| 2004/0260333 A1 | 12/2004 | Dubrul et al. |
| 2005/0015047 A1 | 1/2005 | Shah |
| 2005/0020974 A1 | 1/2005 | Noriega |
| 2005/0033348 A1 | 2/2005 | Sepetka |
| 2005/0038447 A1 | 2/2005 | Huffmaster |
| 2005/0038468 A1 | 2/2005 | Panetta et al. |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0059995 A1 | 3/2005 | Sepetka |
| 2005/0085849 A1 | 4/2005 | Sepetka |
| 2005/0090857 A1 | 4/2005 | Kusleika et al. |
| 2005/0119668 A1 | 6/2005 | Teague et al. |
| 2005/0125024 A1 | 6/2005 | Sepetka |
| 2005/0149111 A1* | 7/2005 | Kanazawa .............. A61F 2/915 623/1.15 |
| 2005/0171566 A1 | 8/2005 | Kanamaru |
| 2005/0187570 A1 | 8/2005 | Nguyen et al. |
| 2005/0267491 A1 | 8/2005 | Kellett et al. |
| 2005/0216030 A1 | 9/2005 | Sepetka |
| 2005/0216050 A1 | 9/2005 | Sepetka |
| 2005/0288686 A1 | 9/2005 | Sepetka |
| 2005/0228417 A1 | 10/2005 | Teitelbaum et al. |
| 2006/0009785 A1 | 1/2006 | Maitland et al. |
| 2006/0009799 A1 | 1/2006 | Kleshinski et al. |
| 2006/0010636 A1 | 1/2006 | Vacher |
| 2006/0030933 A1 | 2/2006 | DeLeggge et al. |
| 2006/0058836 A1 | 3/2006 | Bose |
| 2006/0058837 A1 | 3/2006 | Bose |
| 2006/0058838 A1 | 3/2006 | Bose |
| 2006/0064151 A1 | 3/2006 | Guterman et al. |
| 2006/0149313 A1 | 7/2006 | Arguello et al. |
| 2006/0155305 A1 | 7/2006 | Freudenthal |
| 2006/0155322 A1 | 7/2006 | Sater et al. |
| 2006/0161187 A1 | 7/2006 | Levine et al. |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0282111 A1 | 12/2006 | Morsi |
| 2006/0287701 A1 | 12/2006 | Pal |
| 2007/0088383 A1 | 4/2007 | Pal et al. |
| 2007/0142858 A1 | 6/2007 | Bates |
| 2007/0149996 A1 | 6/2007 | Coughlin |
| 2007/0156170 A1 | 7/2007 | Hancock |
| 2007/0165170 A1 | 7/2007 | Fukuda |
| 2007/0191866 A1 | 8/2007 | Palmer et al. |
| 2007/0198028 A1 | 8/2007 | Miloslavski |

(56) References Cited

U.S. PATENT DOCUMENTS

| | | |
|---|---|---|
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0213765 A1 | 9/2007 | Adams et al. |
| 2007/0225749 A1 | 9/2007 | Martin |
| 2007/0239254 A1 | 10/2007 | Chia et al. |
| 2007/0244505 A1 | 10/2007 | Gilson et al. |
| 2007/0270902 A1 | 11/2007 | Slazas et al. |
| 2007/0288038 A1 | 12/2007 | Bimbo |
| 2007/0293887 A1 | 12/2007 | Okushi et al. |
| 2008/0045881 A1 | 2/2008 | Teitelbaum et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097398 A1 | 4/2008 | Mitelberg |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188928 A1 | 8/2008 | Salahieh |
| 2008/0200946 A1 | 8/2008 | Braun |
| 2008/0215077 A1 | 9/2008 | Sepetka |
| 2008/0221600 A1 | 9/2008 | Dieck et al. |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262528 A1 | 10/2008 | Martin |
| 2008/0262532 A1 | 10/2008 | Martin |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0024157 A1 | 1/2009 | Anukhin |
| 2009/0054918 A1 | 2/2009 | Henson |
| 2009/0069828 A1 | 3/2009 | Martin |
| 2009/0076539 A1 | 3/2009 | Valaie |
| 2009/0105722 A1 | 4/2009 | Fulkerson |
| 2009/0105737 A1 | 4/2009 | Fulkerson |
| 2009/0131908 A1 | 5/2009 | McKay |
| 2009/0163846 A1 | 5/2009 | Aklog et al. |
| 2009/0177206 A1 | 7/2009 | Lozier et al. |
| 2009/0182336 A1 | 7/2009 | Brenzel et al. |
| 2009/0221967 A1 | 9/2009 | Thommen et al. |
| 2009/0270815 A1 | 10/2009 | Stamp et al. |
| 2009/0281610 A1 | 11/2009 | Parker |
| 2009/0292297 A1 | 11/2009 | Ferrere |
| 2009/0292307 A1 | 11/2009 | Razack |
| 2009/0299374 A1 | 12/2009 | Tilson et al. |
| 2009/0299393 A1 | 12/2009 | Martin |
| 2009/0306702 A1 | 12/2009 | Miloslavski |
| 2010/0004607 A1 | 1/2010 | Wilson et al. |
| 2010/0030186 A1 | 2/2010 | Stivland |
| 2010/0030256 A1 | 2/2010 | Dubrul et al. |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0249815 A1 | 9/2010 | Jantzen et al. |
| 2010/0268264 A1 | 10/2010 | Bonnett et al. |
| 2010/0268265 A1 | 10/2010 | Krolik et al. |
| 2010/0292726 A1 | 11/2010 | Olsen et al. |
| 2010/0305604 A1 | 12/2010 | Pah |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield et al. |
| 2011/0009942 A1 | 1/2011 | Gregorich |
| 2011/0022149 A1 | 1/2011 | Cox et al. |
| 2011/0054514 A1 | 3/2011 | Arcand |
| 2011/0054516 A1 | 3/2011 | Keegan |
| 2011/0060359 A1 | 3/2011 | Hannes |
| 2011/0071432 A1 | 3/2011 | Carrillo, Jr. et al. |
| 2011/0077620 A1 | 3/2011 | deBeer |
| 2011/0098683 A1 | 4/2011 | Wiita et al. |
| 2011/0054504 A1 | 5/2011 | Wolf et al. |
| 2011/0125181 A1 | 5/2011 | Brady et al. |
| 2011/0130756 A1 | 6/2011 | Everson, Jr. et al. |
| 2011/0152920 A1 | 6/2011 | Eckhouse et al. |
| 2011/0160763 A1 | 6/2011 | Ferrera et al. |
| 2011/0166586 A1 | 7/2011 | Sepetka et al. |
| 2011/0196414 A1 | 8/2011 | Porter et al. |
| 2011/0202088 A1 | 8/2011 | Eckhouse et al. |
| 2011/0213290 A1 | 9/2011 | Chin et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0218564 A1 | 9/2011 | Drasler et al. |
| 2011/0224707 A1 | 9/2011 | Miloslavski et al. |
| 2011/0264132 A1 | 10/2011 | Strauss et al. |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPama et al. |
| 2012/0089216 A1 | 4/2012 | Rapaport et al. |
| 2012/0101510 A1 | 4/2012 | Lenker et al. |
| 2012/0116351 A1 | 5/2012 | Chomas et al. |
| 2012/0116440 A1 | 5/2012 | Leynov et al. |
| 2012/0143237 A1 | 6/2012 | Cam et al. |
| 2012/0143239 A1 | 6/2012 | Aklog et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0215250 A1 | 8/2012 | Grandfield et al. |
| 2012/0277788 A1 | 11/2012 | Cattaneo |
| 2012/0283768 A1 | 11/2012 | Cox et al. |
| 2012/0296362 A1 | 11/2012 | Cam et al. |
| 2012/0316600 A1 | 12/2012 | Ferrera et al. |
| 2013/0006284 A1 | 1/2013 | Aggerholm et al. |
| 2013/0030461 A1 | 1/2013 | Marks et al. |
| 2013/0046330 A1 | 2/2013 | McIntosh et al. |
| 2013/0046333 A1 | 2/2013 | Jones et al. |
| 2013/0046334 A1 | 2/2013 | Jones et al. |
| 2013/0116774 A1 | 5/2013 | Strauss et al. |
| 2013/0131614 A1 | 5/2013 | Hassan et al. |
| 2013/0144326 A1 | 6/2013 | Brady et al. |
| 2013/0144328 A1 | 6/2013 | Weber et al. |
| 2013/0158592 A1 | 6/2013 | Porter |
| 2013/0184703 A1 | 7/2013 | Shireman et al. |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0281788 A1 | 10/2013 | Garrison |
| 2013/0289697 A1 | 10/2013 | Baker et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0012281 A1 | 1/2014 | Wang et al. |
| 2014/0046359 A1 | 2/2014 | Bowman et al. |
| 2014/0052097 A1 | 2/2014 | Petersen et al. |
| 2014/0081243 A1 | 3/2014 | Zhou et al. |
| 2014/0121672 A1 | 5/2014 | Folk |
| 2014/0128905 A1 | 5/2014 | Molaei |
| 2014/0135812 A1 | 5/2014 | Divino et al. |
| 2014/0180377 A1 | 6/2014 | Bose et al. |
| 2014/0188127 A1 | 7/2014 | Dubrul et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0257362 A1 | 9/2014 | Eldenschink |
| 2014/0276922 A1 | 9/2014 | McLain et al. |
| 2014/0277053 A1 | 9/2014 | Wang et al. |

(56) References Cited

U.S. PATENT DOCUMENTS

| | | |
|---|---|---|
| 2014/0277079 A1 | 9/2014 | Vale et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0364896 A1 | 12/2014 | Consigny |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0080937 A1 | 3/2015 | Davidson |
| 2015/0081003 A1 | 3/2015 | Wainwright et al. |
| 2015/0112376 A1 | 4/2015 | Molaei et al. |
| 2015/0133990 A1 | 5/2015 | Davidson |
| 2015/0142043 A1 | 5/2015 | Furey |
| 2015/0164523 A1 | 6/2015 | Brady et al. |
| 2015/0173783 A1 | 6/2015 | Tah et al. |
| 2015/0238314 A1 | 8/2015 | Börtlein et al. |
| 2015/0250497 A1 | 9/2015 | Marks et al. |
| 2015/0257775 A1 | 9/2015 | Gilvarry et al. |
| 2015/0258270 A1 | 9/2015 | Kunis |
| 2015/0297252 A1 | 10/2015 | Miloslavski et al. |
| 2015/0306311 A1 | 10/2015 | Pinchuk et al. |
| 2015/0313617 A1 | 11/2015 | Grandfield et al. |
| 2015/0320431 A1 | 11/2015 | Ulm, III |
| 2015/0351770 A1 | 12/2015 | Fulton, III |
| 2015/0352325 A1 | 12/2015 | Quick |
| 2015/0359547 A1 | 12/2015 | Vale et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022296 A1 | 1/2016 | Brady et al. |
| 2016/0066921 A1 | 3/2016 | Brady et al. |
| 2016/0074067 A1 | 3/2016 | Furnish et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0121080 A1 | 5/2016 | Cottone |
| 2016/0135829 A1 | 5/2016 | Holochwost et al. |
| 2016/0143653 A1 | 5/2016 | Yale et al. |
| 2016/0151079 A1 | 6/2016 | Aklog et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0228134 A1 | 8/2016 | Martin et al. |
| 2016/0256180 A1 | 9/2016 | Vale et al. |
| 2016/0262880 A1 | 9/2016 | Li et al. |
| 2016/0317168 A1 | 11/2016 | Brady et al. |
| 2016/0346002 A1 | 12/2016 | Avneri et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0065401 A1 | 3/2017 | Fearnot et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172554 A1 | 6/2017 | Bortlein et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0238953 A1 | 8/2017 | Yang et al. |
| 2017/0252043 A1 | 9/2017 | Fuller et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Sethna |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0008407 A1 | 1/2018 | Maimon et al. |
| 2018/0042623 A1 | 2/2018 | Batiste |
| 2018/0193591 A1 | 7/2018 | Jaroch et al. |
| 2018/0235743 A1 | 8/2018 | Farago et al. |
| 2019/0021755 A1* | 1/2019 | Johnson ............... A61B 17/221 |
| 2019/0021759 A1 | 1/2019 | Krolik et al. |
| 2019/0029820 A1 | 1/2019 | Zhou et al. |
| 2019/0029825 A1 | 1/2019 | Fitterer et al. |
| 2019/0046219 A1 | 2/2019 | Marchand et al. |
| 2019/0192175 A1 | 6/2019 | Chida et al. |
| 2019/0209206 A1 | 7/2019 | Patel et al. |
| 2019/0216476 A1 | 7/2019 | Barry et al. |
| 2019/0239907 A1 | 8/2019 | Brady et al. |
| 2019/0255290 A1 | 8/2019 | Snyder et al. |

(56) References Cited

U.S. PATENT DOCUMENTS

| | | |
|---|---|---|
| 2019/0269491 A1 | 9/2019 | Jalgaonkar et al. |
| 2019/0274810 A1 | 9/2019 | Phouasalit et al. |
| 2019/0365411 A1 | 12/2019 | Avneri et al. |
| 2019/0366049 A1 | 12/2019 | Hannon et al. |
| 2020/0038628 A1 | 2/2020 | Chou et al. |
| 2021/0219821 A1 | 7/2021 | Appling et al. |
| 2022/0125450 A1 | 4/2022 | Sirhan et al. |

FOREIGN PATENT DOCUMENTS

| | | |
|---|---|---|
| CN | 103071195 A | 5/2013 |
| CN | 104507380 A | 4/2015 |
| CN | 104905873 A | 9/2015 |
| CN | 105007973 A | 10/2015 |
| CN | 105307582 A | 2/2016 |
| CN | 105726163 A | 7/2016 |
| CN | 106232059 A | 12/2016 |
| CN | 113040865 A | 6/2021 |
| DE | 20 2009 001 951 U1 | 4/2010 |
| DE | 10 2009 056 450 A1 | 6/2011 |
| DE | 10 2010 010 849 A1 | 9/2011 |
| DE | 10 2010 014 778 A1 | 10/2011 |
| DE | 10 2010 024 085 A1 | 12/2011 |
| DE | 10 2011 014 586 B3 | 9/2012 |
| DE | 20 2020 107013 U1 | 1/2021 |
| EP | 2301450 A1 | 3/2011 |
| EP | 2628455 A1 | 8/2013 |
| EP | 3302312 A1 | 4/2018 |
| EP | 3335647 A2 | 6/2018 |
| EP | 3 420 978 A1 | 1/2019 |
| GB | 2498349 A | 7/2013 |
| JP | 9-19438 A | 1/1997 |
| WO | WO 93/04722 A2 | 3/1993 |
| WO | 94/24926 A1 | 11/1994 |
| WO | 97/27808 A1 | 8/1997 |
| WO | 97/38631 A1 | 10/1997 |
| WO | 99/20335 A1 | 4/1999 |
| WO | 99/56801 A2 | 11/1999 |
| WO | 99/60933 A1 | 12/1999 |
| WO | 01/21077 A1 | 3/2001 |
| WO | 02/02162 A2 | 1/2002 |
| WO | 02/11627 A2 | 2/2002 |
| WO | 02/43616 A2 | 6/2002 |
| WO | 02/070061 A1 | 9/2002 |
| WO | 02/094111 A2 | 11/2002 |
| WO | 03/002006 A1 | 1/2003 |
| WO | 03/018085 A2 | 3/2003 |
| WO | 03/030751 A1 | 4/2003 |
| WO | 03/051448 A2 | 6/2003 |
| WO | 2004/028571 A1 | 4/2004 |
| WO | 2004/056275 A1 | 7/2004 |
| WO | 2005/000130 A1 | 1/2005 |
| WO | 2005/027779 A2 | 3/2005 |
| WO | WO 2005/027751 A1 | 3/2005 |
| WO | 2006/021407 A2 | 3/2006 |
| WO | 2006/031410 A2 | 3/2006 |
| WO | 2006/107641 A2 | 10/2006 |
| WO | 2006/135823 A2 | 12/2006 |
| WO | 2007/054307 A2 | 5/2007 |
| WO | 2007/068424 A2 | 6/2007 |
| WO | 2008/034615 A2 | 3/2008 |
| WO | 2008/051431 A1 | 5/2008 |
| WO | 2008/131116 A1 | 10/2008 |
| WO | WO 2009/019664 A1 | 2/2009 |
| WO | 2009/031338 A1 | 3/2009 |
| WO | 2009/076482 A1 | 6/2009 |
| WO | 2009/086482 A2 | 7/2009 |
| WO | 2009/105710 A1 | 8/2009 |
| WO | WO 2009/103125 A1 | 8/2009 |
| WO | 2010/010545 A1 | 1/2010 |
| WO | 2010/046897 A1 | 4/2010 |
| WO | 2010/075565 A1 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 A1 | 9/2011 |
| WO | 2011/110316 A1 | 9/2011 |
| WO | 2012/052982 A1 | 4/2012 |
| WO | 2012/064726 A1 | 5/2012 |
| WO | 2012/081020 A1 | 6/2012 |
| WO | 2012/110619 A1 | 8/2012 |
| WO | 2012/120490 A2 | 9/2012 |
| WO | 2012/156924 A1 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | WO 2014/188300 A1 | 11/2014 |
| WO | 2015/061365 A1 | 4/2015 |
| WO | 2015/134625 A1 | 9/2015 |
| WO | 2015/179324 A2 | 11/2015 |
| WO | WO 2015/179377 A1 | 11/2015 |
| WO | 2015/189354 A1 | 12/2015 |
| WO | 2016/010995 A1 | 1/2016 |
| WO | WO 2017/004234 A1 | 1/2017 |
| WO | WO 2017/097616 A1 | 6/2017 |
| WO | 2018/193603 A1 | 10/2018 |
| WO | WO 2018/178979 A1 | 10/2018 |
| WO | WO 2019/064306 A1 | 4/2019 |
| WO | WO 2019/079296 A1 | 4/2019 |
| WO | WO 2020/139979 A1 | 7/2020 |
| WO | WO 2021/016213 A1 | 1/2021 |
| WO | WO 2021/167653 A1 | 8/2021 |
| WO | WO 2022/020366 A2 | 1/2022 |

OTHER PUBLICATIONS

Struffert, T., et al. "Intravenous flat detector CT angiography for non-invasive visualisation of intracranial flow diverter: technical feasibility" Eur Radiol 21:1797-1801 (2011).

\* cited by examiner

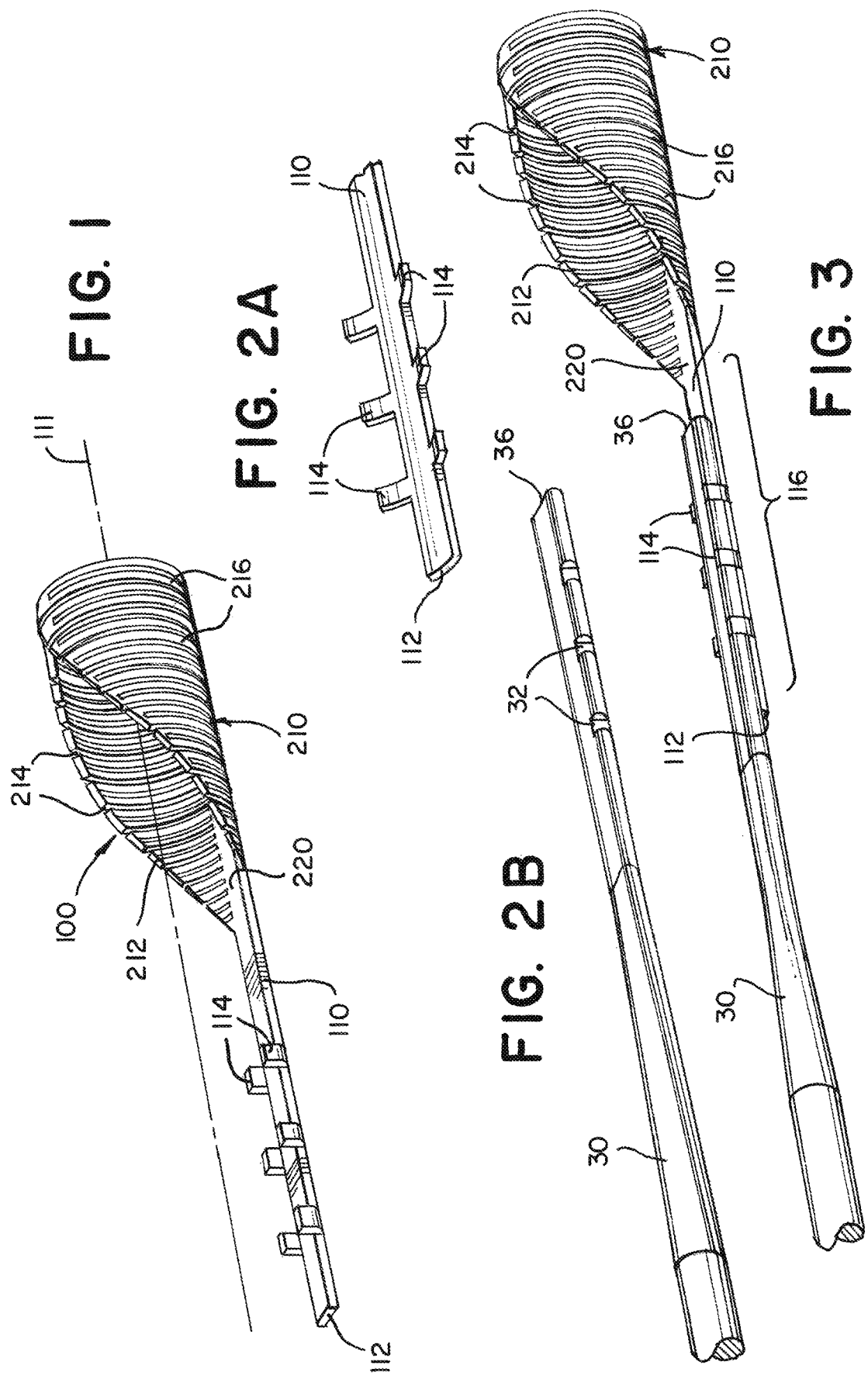

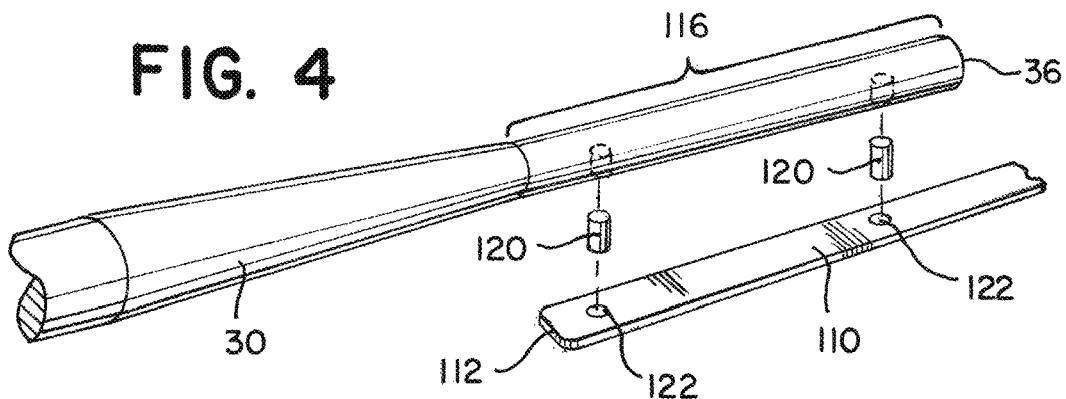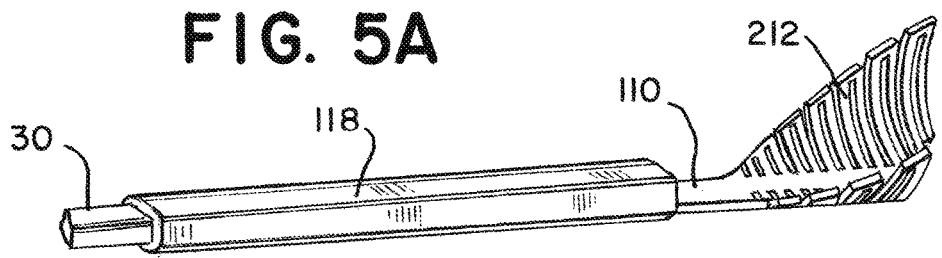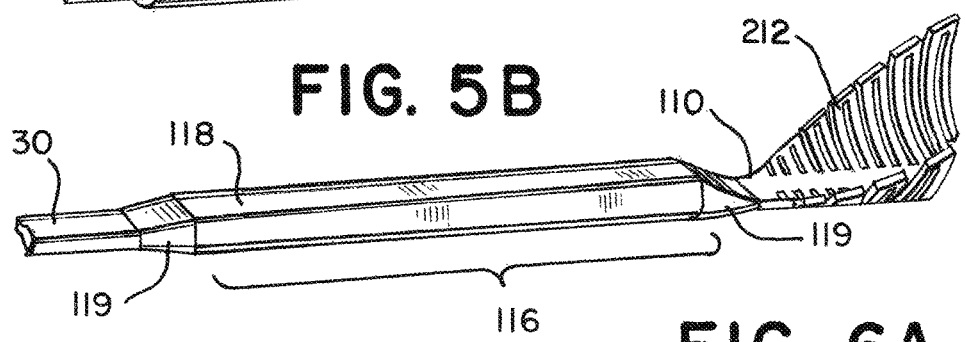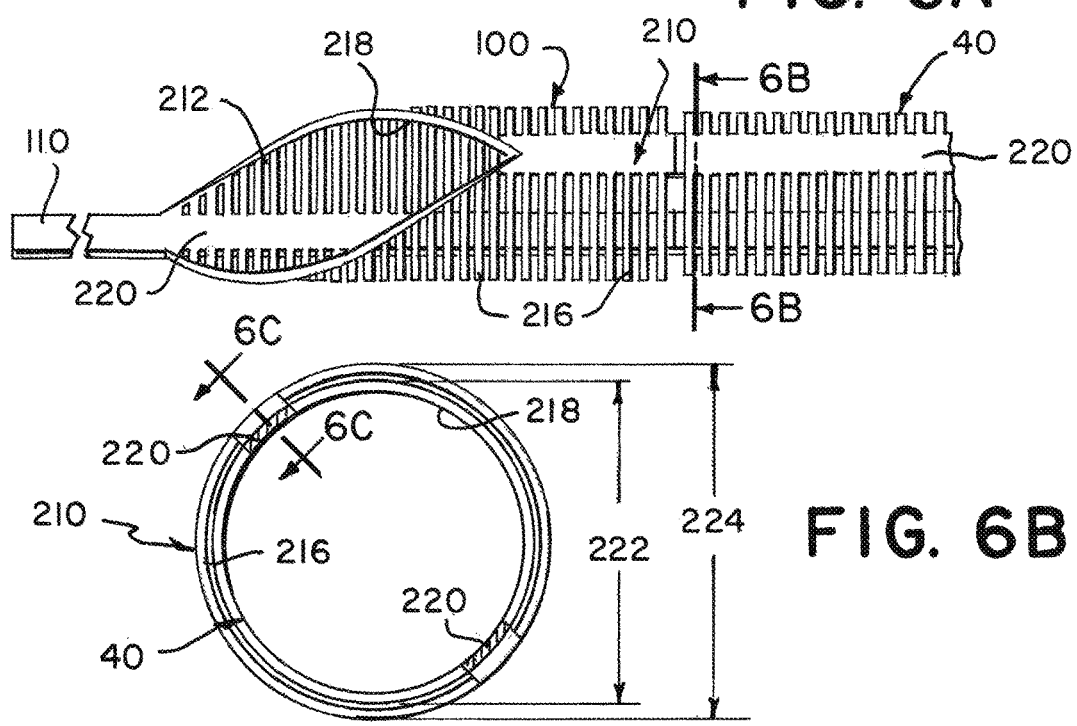

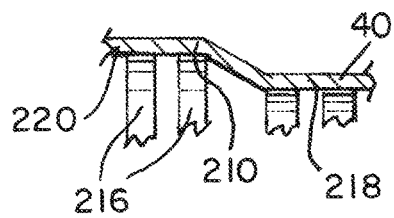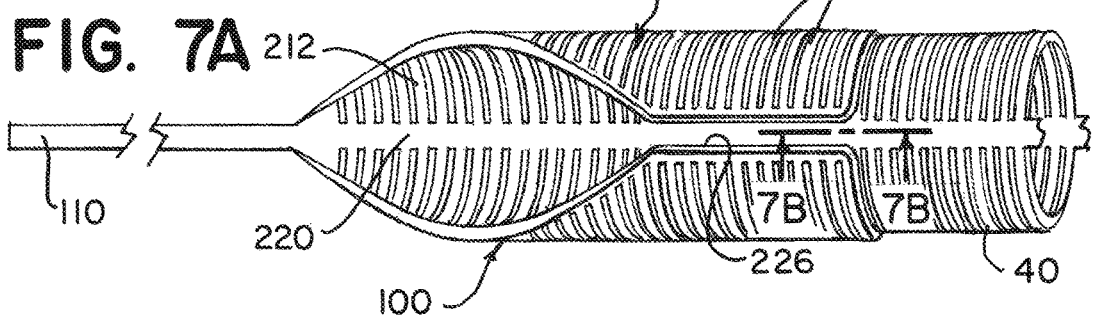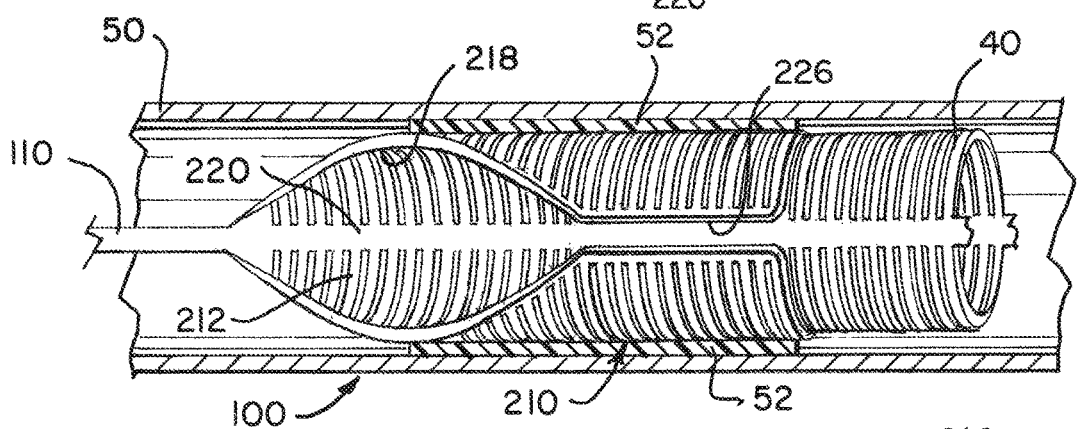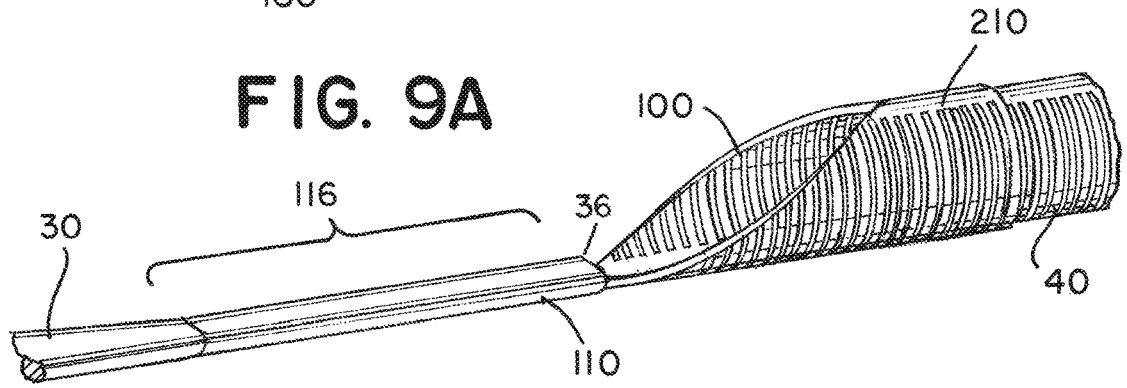

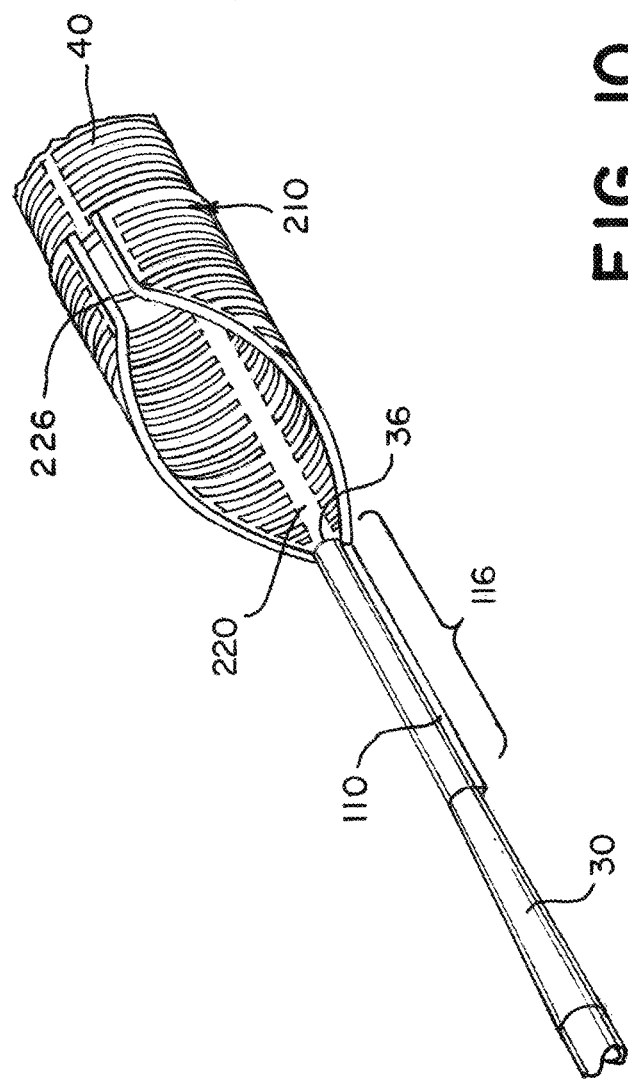
FIG. 9B
FIG. 10
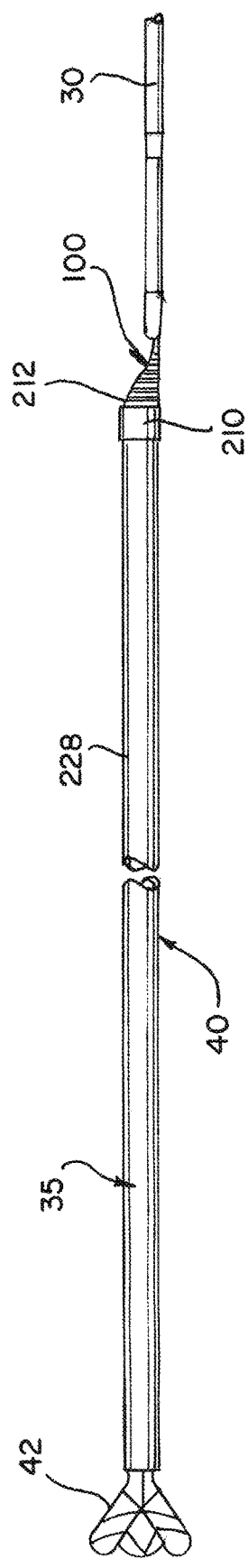

CATHETER PROXIMAL JOINT

FIELD OF THE INVENTION

The present invention generally relates proximal joints for linking a catheter body to a catheter guidewire. More specifically, the present invention relates to joints which provide a gradual stiffness change between the catheter body and guidewire.

BACKGROUND

Aspiration and clot retrieval catheters and devices are used in mechanical thrombectomy for endovascular intervention, often in cases where patients are suffering from conditions such as acute ischemic stroke (AIS), myocardial infarction (MI), and pulmonary embolism (PE). Accessing the neurovascular bed in particular is challenging with conventional technology, as the target vessels are small in diameter, remote relative to the site of insertion, and are highly tortuous. Traditional devices are often either too large in profile, lack the deliverability and flexibility needed to navigate tortuous vessels, or are not effective at removing a clot when delivered to the target site.

In delivering effective devices to the small and highly branched cerebral artery system, conventional catheters must try and balance a number of factors. The catheter must be sufficiently flexible to navigate the vasculature and endure high flexure strains, while also having the axial stiffness to offer smooth and consistent advancement along the route. Newer designs have been introduced which utilize various methods to alter the stiffness between the proximal and distal portions of the catheter. But abrupt stiffness or geometric changes can hinder trackability, introduce significant stress concentrations, and increase the likelihood of device kinking or buckling. This is especially true in regions where different portions of a catheter are manufactured separately and need to be joined securely by mechanical means. Such instances include when a guidewire or shaft for manipulability is connected to the tubular passageway of the catheter by a proximal joint.

Other designs for aspirating clot retrieval catheters have difficulty directing the full suction of aspiration to the volume of fluid and clot distal to the mouth. The suction must be strong enough such that any fragmentation that may occur as a result of aspiration or the use of a mechanical thrombectomy device can be held stationary so that fragments cannot migrate and occlude distal vessels. However, when aspirating with traditional catheters, such as a fixed-mouth catheter or a catheter which does not seal with an outer catheter, a significant portion of the aspiration flow ends up coming from vessel fluid proximal to the tip of the catheter, where there is no clot. This significantly reduces aspiration efficiency, lowering the success rate of clot removal.

Solutions, such as highly flexible catheter body designs, are often of a reduced diameter incapable of generating the required suction force. Improved aspiration designs, such as those with expandable members or separate suction extensions, typically lack the flexibility to navigate the neurovascular intact.

The present design is aimed at providing an improved proximal joint giving better performance characteristics to an aspirating retrieval catheter which addresses the above-stated deficiencies.

SUMMARY

It is an object of the present design to provide systems, devices, and methods to meet the above-stated needs. It is therefore desirable for an aspiration clot retrieval catheter with a proximal joint for transitioning from a profiled guidewire to a tubular support structure with a large lumen for aspiration and the passing of other devices for performing mechanical thrombectomy procedures. The transition joint can be low-profile and sufficiently flexible in multiple directions for deliverability to the target site, while providing a smooth transition in stiffness between catheter segments. The transition joint can include an outer seal that interacts with an outer catheter such that an aspiration source is connected to the proximal end of the outer catheter has a direct fluidic connection to the distal mouth of the aspiration clot retrieval catheter. The seal ensures there is little or no loss in negative pressure between the aspiration source and the mouth.

The transition can be a proximal joint for linking a catheter with a tubular body and a guidewire for manipulation. The proximal joint can have a distal tubular section defining an internal lumen therethrough and a proximal strut extending proximal to the distal tubular section. The distal tubular section can include one or more axial spines, a plurality of ribs along the one or more spines and disposed around a longitudinal axis, and a tapered opening. The internal lumen of the distal tubular section can be shared with the lumen of the tubular catheter body used for passing devices and directing aspiration. The proximal strut can be integral with and extend proximally from one of the one or more spines. The strut can be configured to overlap a distal portion of the guidewire to form a zone for mechanically locking the guidewire to the catheter body. At least a portion of the distal tubular section can be coated with a flexible and highly elastic polymeric cover which can be stretched to the contours of the tubular section and catheter body.

The distal tubular section can be formed integrally with the catheter body and help support the outer cover or membrane. For example, the structures could be cut from a single hypotube. Alternately, the tubular section could be a braided or coiled structure of sufficient density to support the cover. At least a portion of the tubular section of the proximal joint can be of a diameter larger than the diameter of the catheter body and sized to seal with an outer catheter such that aspiration is directed to the distal tip of the aspirating clot retrieval catheter. The ribs of the distal tubular section could be cut to this larger diameter, or they could be enlarged through plastic deformation. If constructed of a shape memory alloy, the tubular section could include a longitudinal slot or slots, and/or the ribs could be machined at an acute angle to the longitudinal axis such that they could be heat set to a larger diameter prior to applying the outer polymer cover or jacket. To further increase the flexibility of the tubular section, the perimeter of the tapered opening could have notches or cutouts to make the region more compliant in bending.

The guidewire can have a flattened or rounded distal end depending on the desired interface at the proximal joint of the catheter. The guidewire can be formed with features that interlock with features of the proximal strut of the catheter tubular support section such that the features form a mechanical constraint between the support structure and the guidewire. For example, locking arms could extend laterally away from the central proximal strut and could be configured to engage corresponding notches in the guidewire shaft within the locking zone. In another example, one or more pins could extend radially from the proximal strut and be configured to engage with thru holes or pockets in the locking zone of the guidewire shaft. The pins and pockets could also be divided between the proximal strut and guidewire and spaced for a smooth stiffness transition through the locking zone. These features deliver thrust from the user while preventing longitudinal translation between the guidewire and the proximal strut.

Heat-shrink, reflowed polymers, and/or adhesives can be used to reinforce the connection between the guidewire and tubular support section. The reinforcement can prevent a disengagement of the mechanical lock between the guidewire and catheter body. One or more polymer jacket could extend through at least a portion of the locking zone or could extend the entire length of the guidewire. The jacket or jackets could be made from a low-friction material and the edges could be tapered to be flush with the proximal strut and guidewire surfaces such that auxiliary devices used in the procedure are not snagged at the interface. Multiple jackets of differing stiffnesses could be used at different longitudinal sections of the guidewire and locking zone.

In another example, a proximal joint for connecting a guidewire to a catheter body can include a tubular support structure formed integrally with and proximal to the catheter body and a proximal strut extending proximal to the support structure and configured to mate with a distal portion of the guidewire. The tubular support structure can have a maximum radial size larger than a maximum radial size of the catheter body and sized to seal with the inner diameter of an outer delivery catheter. The support structure can be fabricated at the maximum radial size or it can be deformed to flare radially outward. Alternatively, a separate seal component can be provided with the joint which expands or swells to direct aspiration to the distal tip of the clot retrieval catheter and isolate fluid proximal of the seal component. In another embodiment, a highly flexible proximal joint can be positioned over a proximal section of the distal luminal catheter body and may include mechanical lock features similar to those disclosed between the guidewire and proximal joint. By mating a highly flexible section of the tubular section of the proximal joint with a highly flexible proximal section of the distal luminal catheter body, impact to the overall stiffness can be minimized.

A cover can be disposed around at least part of the support structure and can extend distally to enclose the catheter body. The tubular support structure can have one or more axial spines and a series of loop ribs to support the cover and define a hollow internal lumen for the catheter. The lumen can be coated with a low-friction liner to facilitate the passage of ancillary devices through the catheter. The cover could be reflowed, adhered, and/or stitched to the loop ribs of the support structure. The cover could further be coated with a low-friction film to improve trackability and mitigate the risk of binding when delivered through an outer catheter.

The proximal strut can be aligned with one of the one or more axial spines extending longitudinally down the support structure. The proximal strut can have locking arms that can extend laterally from the strut and bend to engage with notches machined into the distal end of a flattened guidewire. In another example, the proximal strut can have a concave face for receiving a guidewire with a rounded cylindrical distal end. A reinforcing polymer sleeve can be disposed around at least a length of the proximal strut and a length of the guidewire to bolster the joint and dampen the stiffness transition between the guidewire and support structure as well as provide a smooth profile for unhindered passage of ancillary devices.

Additionally, a clot retrieval catheter for capturing an occlusive thrombus can have a tubular suction section, a guidewire, and a proximal joint for securing the tubular suction section to the guidewire. The proximal joint of the catheter can include a distal tubular structure, a proximal strut extending in a proximal direction from the tubular structure, and a polymeric jacket bonding and securing a length of the proximal strut to a length of the guidewire. The proximal strut can be formed integrally with the distal tubular structure such that there is no abrupt stiffness change or geometric stress concentration. The proximal joint can include features configured for mechanically securing the proximal strut and a distal portion of the guidewire, or the polymer jacket can be used to fix the position of and bond overlapped sections of the proximal strut and guidewire. This bond can allow thrust and torque applied to the guidewire by the user to be transmitted to the distal tubular section of the proximal joint and the distal luminal portion of the catheter body.

Where a polymer jacket is used, the jacket can be applied over just the overlapping portion of the proximal strut and guidewire or could continue proximally a further length of the guidewire. A low-friction coating can be applied to the jacket and/or guidewire, or lubricious particles can be impregnated within the jacket for easier navigation within an outer catheter.

The distal tubular structure can include a tapered opening at the proximal end, one or more axial spines along the longitudinal axis. A plurality of loop ribs can extend around the longitudinal axis from the one or more spines and define a hollow inner lumen for the distal tubular structure. The distal tubular structure and the catheter body tubular section can be formed integrally, such as when machined from a hypotube or with one or a series of cylindrical braids, such that the hollow inner lumen can be shared between the segments. When constructed in this fashion the magnitude of the stiffness transition between the distal tubular structure and the catheter body tubular section can be mitigated.

The distal tubular structure can be formed with features that allow some or all of the structure to be enlarged through permanent plastic deformation or a heat set. These features allow the enlarged region to have a greater diameter than the distal tubular catheter body. An enlarged region can expedite the passage of thrombectomy devices and/or can form a seal with an outer delivery catheter for the efficient direction of suction to the distal tip of the clot retrieval catheter. This sealed configuration takes advantage of the large proximal lumen of the outer catheter to enhance aspiration through the clot retrieval catheter.

For example, an enlarged section could be formed from one or more longitudinal slots incorporated into the distal tubular structure such that the ribs adjacent to the slot are not constrained tangentially so they can be deformed, or heat set to a larger radial size. As an alternative, the ribs of the distal tubular section could be formed or machined from a shape memory alloy at an angle less than 90 degrees to the longitudinal axis. These ribs could subsequently be heat set to an angle largely perpendicular to the longitudinal axis to achieve an enlarged section of the distal tubular structure. In a further example, the distal tubular section could effectively be enlarged through a hydrogel coating which swells in an isotropic fashion with hydration to achieve a seal with the outer delivery catheter.

If a complete seal is not desired, a flow restrictor can be used between the outer catheter and the clot retrieval catheter. The flow restrictor could have bristles, a dense framework, or some other form which could inhibit flow. The flow restrictor can be located on the outer surface of the distal tubular structure of the clot retrieval catheter.

The clot retrieval catheter can further have an expanding distal tip which can provide a larger opening into which a clot retrieval device and a captured thrombus can be withdrawn, lessening the risk of the tip shearing or dislodging the thrombus or fragments of the thrombus from the retrieval device and also providing a gradual compression of clot as the clot is drawn into the mouth of the clot retrieval catheter through aspiration, use of a retrieval device, or through a combination of aspiration and use of a retrieval device. Fragmentation can occur with catheters having a distal mouth with a cross-section smaller than that of the thrombus itself or if the clot enters the mouth of the catheter at an offset position.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this invention are further discussed with the following description of the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation. It is expected that those of skill in the art can conceive of and combining elements from multiple figures to better suit the needs of the user.

FIG. 1 is an isometric view of a proximal joint for an aspiration clot retrieval catheter according to aspects of the present invention;

FIGS. 2A-2B show an example locking mechanism for the proximal strut and guidewire using locking arms, according to aspects of the present invention;

FIG. 3 shows the proximal joint with the engagement of the proximal strut and guidewire using the locking mechanism of FIG. 2A-2B, according to aspects of the present invention;

FIG. 4 shows another example locking mechanism for the proximal strut and guidewire using locking pins, according to aspects of the present invention;

FIG. 5A illustrates a polymer jacket applied over the locking zone of the proximal joint according to aspects of the present invention;

FIG. 5B illustrates a polymer jacket with tapered ends applied over the locking zone of the proximal joint according to aspects of the present invention;

FIG. 6A is a view of a proximal joint having two spines and an enlarged tubular section according to aspects of the present invention;

FIG. 6B is a cross-section view of FIG. 6A according to aspects of the present invention;

FIG. 6C is a cross-section view of FIG. 6B showing the radial transition between the enlarged tubular section and the catheter body according to aspects of the present invention;

FIG. 7A shows an alternative proximal joint with an enlarged tubular section according to aspects of the present invention;

FIG. 7B is a cross-section view of FIG. 7A according to aspects of the present invention;

FIG. 8 shows a proximal joint with an enlarged tubular section within an outer catheter according to aspects of the present invention;

FIG. 9A illustrates a proximal joint where the guidewire in the locking zone has a flattened, rectangular profile according to aspects of the present invention;

FIG. 9B illustrates a proximal joint where the guidewire in the locking zone has a rounded, cylindrical profile according to aspects of the present invention;

FIG. 10 is an overall view of a catheter with a flexible polymeric cover disposed around an expansile tip, a tubular body, and a portion of the proximal joint according to aspects of the present invention;

DETAILED DESCRIPTION

Figure 11A:
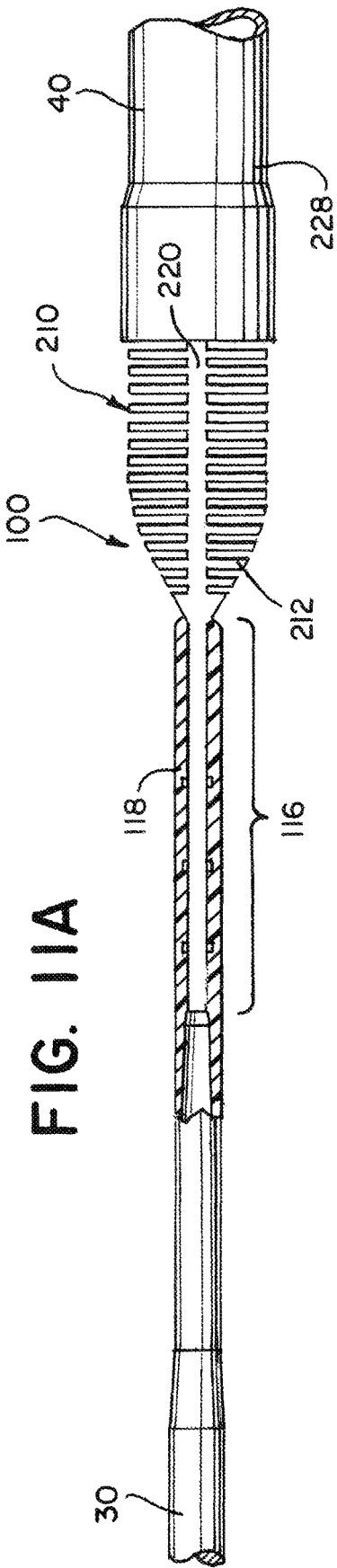
FIG. 11A is a top view of a proximal joint where a reinforcing polymer jacket covers a length of the catheter guidewire and locking zone, according to aspects of the present invention.

Specific examples of the present invention are now described in detail with reference to the Figures, where identical reference numbers indicate elements which are functionally similar or identical. The examples offer many improvements over traditional catheters, such as excellent thrust response through a profiled guidewire, characteristics to tailor the stiffness of different catheter segments through a proximal joint, and a smooth transition in stiffness between the guidewire segment and the distal tubular body of the catheter. In the case of stroke intervention procedures, where vessels in the neurovascular bed are small and very tortuous, combining a tailored stiffness profile with smooth transitions inhibits kinking and binding while offering distinct deliverability advantages. These improvements can lead to safe and more rapid access of a catheter and other devices to complex areas of the intercranial arteries to remove occlusions and shorten procedure times.

Accessing the various vessels within the vascular, whether they are coronary, pulmonary, or cerebral, involves well-known procedural steps and the use of a number of conventional, commercially available accessory products. These products, such as angiographic materials, rotating hemostasis valves, and guidewires are widely used in laboratory and medical procedures. When these or similar products are employed in conjunction with the system and methods of this invention in the description below, their function and exact constitution are not described in detail.

Referring to the figures, in FIG. 1 there is illustrated a proximal joint 100 for connecting a body and a guidewire of an aspirating clot retrieval catheter according to this invention. The proximal joint can have a distal tubular section 210 which can include a plurality of loop ribs 216 disposed along one or more axial spines 220 and defining a longitudinal axis 111. The distal tubular section can taper proximally to form a tapered opening 212 which can serve as an entrance through which other treatment devices, such as a microcatheter and stentriever, can access the lumen 218 of the tubular section. The axially tapering profile of the opening relative to the longitudinal axis, as shown in the figure, can help to facilitate the introduction of these devices to the intraluminal section of the catheter. Alternatively, an opening at a right angle can be used if desired. The opening 212 can have notches or breaks 214 cut into the perimeter to reduce the bending stiffness of the opening as it transitions to one of the spines 220 to a tubular profile.

The terms distal tubular section, tubular support structure, and distal tubular structure as used herein are intended to refer to the same structure and are used interchangeably. It can be appreciated that other appropriate verbiage could also be substituted.

The proximal joint 100 can have an axial member which extends proximally from the distal tubular section 210 where the tapered opening 212 transitions away from the suction body of the catheter. The member can be a proximal strut 110 designed to provide an interface with which to link a pushable guidewire 30 to the catheter. In one example, the strut member can be a cylindrical or rectangular strut which can form a continuous extension from one of the spines 220 of the distal tubular section. In another example, the strut can be a flat wire or coil which is embedded into a polymeric anchor of the distal tubular section. The wall of the tubular section could be formed with a thicker section along one edge of the circumference to serve as the anchor and reinforce the interface.

The loop ribs 216 and the one or more axial spines 220 of the distal tubular section 210 could be formed from laser-cutting a hypotube or similar tube stock. Commonly used hypotube materials include Nitinol and familiar medical-grade stainless-steel alloys like 304 and 316. In one example, the distal tubular section is formed integrally with the proximal strut 110 and the tubular luminal body of the catheter. This configuration allows for one of the one or more spines 220 to continue proximal of the tapered opening 212 as a continuous proximal strut 110 member. A continuous spine and proximal strut combination could yield excellent pushability characteristics while maintaining a gentler bending stiffness transition between the proximal strut and the distal tubular section.

Tailoring of the stiffness and changes in stiffness for the catheter is important for situations where the distances and tortuosity can be significant, such as when it must be advanced from a patient's inner thigh, over the cardiac arch, and up into the neurovascular vessels inside the skull. Adjusting the cuts in a hypotube which form the ribs 216 and spines 210 of the distal tubular section 210 can be used to tailor this stiffness. For example, the ribs can be cut to various widths and spacing density. The cuts could be circumferentially continuous and terminate on either side of an axial spine 220, or the cuts could be discontinuous in a repeating or non-repeating pattern around the circumference of the tubular section. If discontinuous cuts are aligned axially, they can form one or more additional axial spines 220 to bias bending and flexing planes of the catheter. As a further example, if circumferentially discontinuous cuts are mixed and aligned with circumferentially continuous cuts, as shown in FIG. 1, they can form a discontinuous axial spine.

The axial spine or spines 210 themselves could be formed or cut at various thicknesses. A thicker spine could provide more column strength and axial stiffness for better kink resistance and insertion and retraction performance of the catheter. Conversely, a spine of a thinner thickness could provide more flexibility in bending for navigating tortuous areas of the vasculature. The spine or spines could also taper in thickness along the length of its axis in order to incorporate both of these advantages. A tapered spine or spines could be made stiffer proximally for good pushability characteristics and very flexible distally to allow the tubular section to contort and twist around the vessel paths.

In another example, the distal tubular section 210 of the proximal joint 100 can have a metal and/or polymer strand construction formed into a braided or coiled structure. The strands can form a radial array as a continuous structure with the tubular catheter body in order to approximate a singular support piece, similar to that of a laser-cut hypotube. The strands of the distal tubular section can be formed on a straight mandrel so that they flare radially outward to form a seal with the inner diameter of an outer or intermediate catheter. Instead of a seal, the strands form a braided or coiled structure of sufficient density that fluid flow is substantially impeded between the exterior and interior of the tubular section, such that a perfect seal is not necessary.

The proximal strut 110 can be formed with features that grip features of the catheter guidewire 30 such that the features form a mechanical lock between the support structure and the guidewire. The features can be chosen such that they prevent axial translation but do not inhibit the joint from bending or twisting about the longitudinal axis 111. For example, lateral material extensions can flank the proximal strut to form locking arms 114. The locking arms can be laser-cut such that they are integral with the proximal strut and radially perpendicular to the axis as shown in FIG. 2A. When the proximal joint is assembled, the locking arms can be heat set or plastically deformed to a position radially inward in order to engage with complimentary notches 32 or slots machined into the surfaces near the distal end 36 of the guidewire 30, as illustrated in FIG. 2B.

The guidewire 30 itself can have any of a number of reasonable cross-sectional profiles which can be different for different axial lengths of the guidewire. The guidewire can taper to a smaller profile or circumference at the distal end 36 of the guidewire, such that when joined with the proximal strut 110 or mating member of the proximal joint the sections share a composite stiffness more approximate that of wider proximal sections of the guidewire.

In general, the guidewire 30 can be a solid wire, braid, coil, or the like that provides for the smooth transmission of thrust and retraction forces to the tubular section 210 of the proximal joint 100 of the catheter, allowing the catheter to move with the tubular section relative to an outer catheter (not illustrated) in the assembled clot retrieval system. The guidewire can have a length longer than that of an outer catheter so that the proximal end of the guidewire extends from the proximal end of the outer catheter. The guidewire can be constructed of a high-modulus polymer, or any of a range of biocompatible metallic options such as titanium, Nitinol, or stainless-steel alloys as long as they have sufficient proportions of flexibility and column stiffness necessary to navigate requisite areas of the vasculature.

The significant change in geometry between the low-profile guidewire 30 and the elongate tubular section of the catheter can lead to substantial bending strains and/or stresses where the transition takes place. Independently, the proximal strut 110 of the proximal joint 100 and the portion of the guidewire 30 approximate the guidewire distal end 36 both resemble cantilever beams. To create a more gradual stiffness transition between the guidewire and proximal joint, a section of the guidewire can overlap longitudinally with a section of the proximal strut as illustrated in FIG. 3. This overlap can define a locking zone 116 designating an engagement length over which the joint becomes a composite beam. The locking arms 114 or other geometric features of the proximal strut can then engage to secure the interface.

Another design for mechanically locking the proximal joint can be seen in FIG. 4. In this example, the guidewire utilizes cylindrical locking pins 120 extending radially within the locking zone 116 near the distal end 36 of the guidewire 30. The locking pins can be configured for insertion into corresponding locking pockets 122 recessed into the proximal strut 110. The joint could be made more secure by having the locking pins and locking pockets interface as a snap fit or interference fit. Alternately, the pins could be machined as extensions of the proximal strut. Rounded pins can reduce the stress concentrations inherent at geometric corners and provide a proximal joint interface with additional torque carrying capacity.

It should be noted that the examples of the proximal joint locking systems shown and described herein are a small number of available designs, and one of skill in the art will recognize that many other configurations are possible beyond what is explicitly described.

FIG. 5A shows an example of a proximal joint where a polymer jacket 118 has been heat-shrunk or reflowed over the length of the locking zone 116 to reinforce the mechanical joint between the proximal strut 110 and the catheter guidewire 30. The polymer jacket can further blend the geometric transition at the proximal and distal ends of the locking zone 116. The jacket can extend proximally along the guidewire beyond the edge of the locking zone and distally to the very proximal face of the enlarged tapered opening of the tubular section to completely bond and reinforce the joint assembly. As illustrated in FIG. 5B, the edges of the jacket 118 can be made flush with the corresponding surfaces of guidewire and proximal strut so that there are no lips or corners of the locking zone interface or jacket which could otherwise snag or inhibit ancillary devices as they are delivered through the clot retrieval catheter.

In an alternative example, the guidewire 30 or the proximal strut 110 could be shaped to fit inside a hollow housing of the opposite number and a press-fit or adhering element used to secure the mating surfaces. A polymer jacket 118 could then be reflowed over the locking zone 116 to form a more continuous external profile. Additionally, adhesives could also be used with or without polymer jackets to constrain and/or fortify the proximal joint between the catheter The interface of the guidewire 30 with the proximal strut 110 of the proximal joint 100 can serve the purpose of both securing the components together while also developing into the shape of the tapered opening 212 of the distal tubular section 210. Similar to other examples, the tapered opening 212 can have notches or breaks 214 machined into the perimeter to reduce the bending stiffness at the opening. The exterior of the tubular section can be sized to form a desired interface between the aspirating clot retrieval catheter and an outer or intermediate catheter. The tubular section can form a seal with the inner surface of the outer catheter, such that an aspiration source connected to the proximal end of the outer catheter has a direct connection to the distal mouth of the aspirating clot retrieval catheter with little or no negative pressure loss between the source and the mouth.

One example of a proximal joint 100 for an aspirating clot retrieval catheter that is capable of sealing with an outer catheter is shown in FIG. 6a. The distal tubular section 210 of the proximal joint can still be formed integrally with the tubular catheter body 40, such as when both are cut from the same hypotube or formed from a continuous coiled structure. The proximal strut can also be cut as a continuous extension of one of the catheter spines 220. The catheter body can have multiple designs, or be cut in different sections, to control the stiffness profile along the length of the body to minimize insertion and retraction forces of the catheter. Features can also be incorporated which bias bending about certain planes or encourage twisting to reduce the imparted strains. In this way the catheter will maintain excellent lateral flexibility but will not tend to expand or kink in compression.

A cross-sectional view from FIG. 6A through a part of the tubular section of the catheter is illustrated in FIG. 6B. The distal tubular section 210 can generally be distinguishable from the catheter body 40 by having an outer diameter 224 larger than the outer diameter 222 of the catheter body extending downstream along the catheter spine or spines 220. example illustrated in FIG. 6A has two axial spines spaced 180 degrees apart. Use of a double spine yields good thrust and trackability characteristics to aid in advancing the catheter to the target location, while reducing the possibility of elongation under tensile loads, such as when a large clot is retracted into the mouth of an expandable tip at the distal end of the catheter or an outer catheter. Spacing the spines 180 degrees apart also biases the catheter body and tubular section to flex about a single plane in order to transmit a more balanced push force to the catheter. The created bending plane passes through the spines of the dual spine layout of FIG. 6B. The stepped profile of a spine at the transition between the catheter body 40 and the enlarged outer diameter of the proximal joint tubular section 210 is illustrated in cross-section in FIG. 6C.

FIG. 7A illustrates a further example of a proximal joint 100 formed integrally with the tubular catheter body 40 where both structures are cut from the same hypotube. Similar to FIG. 6A, the adjacent catheter body 40 can have a stepped down diameter from that of the tubular section 210 of the proximal joint. In these examples, the enlarged tubular section can be formed in multiple ways. In one case, the loop ribs 216 of the tubular section can be machined at an angle less than 90 degrees to the longitudinal axis so that the ribs can be heat set to an angle approximately perpendicular to the axis to achieve the enlarged section 210 proximal to the catheter body 40. Alternately, the machined pattern of the tubular section 210 can include one or more longitudinal slots 226 so that the ribs are not constrained tangentially around the circumference. The ribs can then be reset or deformed to a position radially outward of the more distal portion of the catheter body to achieve an enlarged diameter.

The longitudinal slot or slots 226 could be machined such that they are aligned with or offset from any of the one or more axial spines 220. If aligned, one or more of the spines could be discontinuous at the transition interface between the enlarged tubular section 210 and the catheter body 40, as seen in the top view of FIG. 7A and in FIG. 7B. A discontinuous spine can help the catheter proximal joint further transition the bending stiffness between the downstream catheter body and the connection between proximal strut 110 and the catheter guidewire.

Alternately, the distal tubular section 210 can taper gradually inward from the maximum radial size 224 to assume the outer diameter 222 of the catheter body 40. The catheter body in these examples can be balanced to transmit a substantial suction force while being capable of further reach into more distant and narrow neurological vessels. The diameter 222 of the catheter body shown in FIGS. 7A and 7B could also be an intermediate diameter, where the catheter body is formed from further tubular sections which step down to a progressively smaller size, giving enhanced bending flexibility to distal regions of the body. The distal end of the catheter body could have an expandable member to recover a large distal mouth for aspirating a clot.

The interface between the outer diameter of the enlarged tubular section 210 of the proximal joint 100 and the inner diameter of a section of the outer catheter 50 can be seen in FIG. 8. When the catheter has been longitudinally positioned for the procedure, this junction can reduce or eliminate any flow between the surfaces so that essentially all of the suction flow passes through the shared lumen 218 of the tubular section and catheter body 40 to the distal tip of the clot retrieval catheter. The enlarged tubular section can be positioned by the user at a desired axial location of the outer catheter such that an adequate seal and functionality are obtained.

A seal 52 between the proximal joint 100 and the outer catheter 50 can be created in several ways. The distal tubular section 210 can be enlarged to extend radially outward to generate a circumferential sealing surface with the inner wall of the outer catheter 50. The ribs or the tubular section 210 can be cut or heat set to a larger diameter prior to applying an outer polymer jacket. Slots or strain relief features machined into the cut pattern of the tubular section can also be used to create a geometry that will deform or be effectively spring-loaded to a larger outer diameter. As an alternative, the outer jacket or membrane could be formed with a soft elastomeric rib disposed around the tubular section 210. The maximum radial dimensions can thus be designed to interface with commonly sized commercial outer catheters such that a seal is developed at the contact surface.

Alternatively, a portion of the tubular portion 210 of the proximal joint 100 can be enlarged through coating with a hydrogel that swells with hydration in order to achieve a seal with the inner surface of the outer catheter 50. Hydrogels offer the advantages of biocompatibility, relative tackiness as an adhesive, and flexibility enough to accommodate comparative motion of the joint while maintaining molecular stability when swelled.

Proximal to a seal, the shape and profile of the overlap and the contact surface developed within the locking zone 116 of the proximal joint 100 can be tailored for both the guidewire 30 and the proximal strut 110 to eliminate stiff transitions inherent with assembly of multiple parts. Components which overlap can form weak transitions which are prone to buckling or kinking when butted together. A smoother contact profile between mating parts is typically desirable, so in the illustrated example of FIG. 9A the guidewire transitions from a cylindrical profile to a flattened wire profile near the distal end 36 in order align with the proximal strut extending from a spine 220 of the laser-cut of tubular support section 210. In a different example, the catheter guidewire within the locking zone can maintain the substantially cylindrical structure of FIG. 9B up to the distal end 36. The corresponding mating surface of the proximal strut within the locking zone can have a face which forms an extended concave arc with a matching radius of curvature.

The axial length of the locking zone 116 and the type of mechanical locking joint used will also determine the final bending stiffness properties of the proximal joint. It can be appreciated that longer locking zones allow more material to carry the bending load and thus a more gradual change in stiffness while reducing the bend radius capacity of the joint.

A construction view for a suitable aspirating clot retrieval catheter 35 for thrombectomy procedures with aspects of the current design is illustrated in FIG. 10. The catheter can comprise an expandable tip 42 with a collapsed delivery configuration and expanded deployed configuration at the distal end. The tip can seal with the walls of an occluded vessel when expanded to direct efficient aspiration. A proximal joint 100 with a tubular section 210 can transition an elongate suction catheter body 40 to a guidewire 30 serving as a control element for the catheter. In some cases, the overall length of the guidewire 30 can be substantially greater than the length of the tubular catheter body 40 such that the column strength of the guidewire offers excellent pushability characteristics over the majority of the insertion length. The proximal joint 100 manages the transition between these lengths to mitigate the likelihood of binding or kinking at this interface in the complex anatomy of the neurovascular.

An outer liner or cover 228 can be disposed around at least a portion of the expandable tip 42, catheter body 40, and the tubular section 210 of the proximal joint 100. The cover can be a membrane constructed of a highly elastic material, such as a low-modulus elastomer, so that it stretches as the tip expands and can follow the contours of the underlying framework of the catheter. The cover can run the entire length of the catheter body and tubular section or it can terminate at or some distance distal to the tapered opening 212.

The exact composition and structure of the cover 228 can be configured depending on the needs of the procedure. The cover can be used for creating the seal with an outer catheter, or it can be used to provide a lubricious surface for limiting the transmission forces needed to deliver and deploy the catheter 35. The cover could also be used to adjust the desired stiffness qualities of differing axial portions of the catheter.

If the support framework of the catheter body 40 and tubular section 210 is cut from a hypotube, spaces, slots, or patterns can be laser-cut into the outer surface of the hypotube and the cover 228 could be reflowed or injection molded into the spaces during manufacturing. The cover could be adhered to the struts and ribs using heat and/or adhesive. The spines and ribs of the support structure could also be embedded or encapsulated in a polymeric tube. The tube could be embedded with reinforcing metallic elements or particles with low-friction characteristics to reduce the static and dynamic coefficients of friction for the outer surfaces. A low-friction liner, such as a fluoropolymer, can also extend through the lumen 218 around the inner diameter of the tubular section 210 and the connecting section of the catheter body 40 to facilitate the feeding of other devices through the aspirating clot retrieval catheter.

Alternatively, the cover 228 could also be a formed from a series of polymer jackets. Different jackets or sets of jackets could be configured in an axial series to transition the overall stiffness of the catheter from being stiffer at the proximal end to extremely flexible at the distal end. Alternately, the polymer jackets of the cover could be radially disposed about the support tube in order to tailor the material properties through the thickness. The expandable tip 42 could have the same or a separate jacket or jackets that can be dip coated and can butt against or extend to be situated under or over the jackets of the support tube.

Figure 11B:
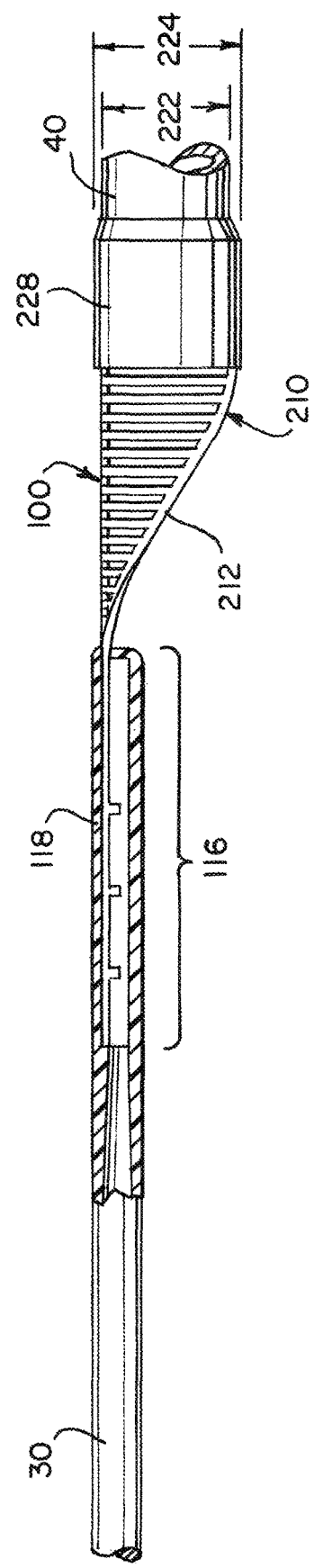
FIG. 11B shows a side view of the proximal joint of FIG. 11A according to aspects of the present invention.

FIG. 11A and FIG. 11B show top and side views of the proximal joint 100 from the catheter 35 of FIG. 10. The polymeric membrane cover 228 can be disposed around the distal catheter body 40, but the cover can also enclose all, some, or none of the tubular section 210 of the proximal joint 100. If the membrane is to enclose only a part of the tubular section, the membrane proximal edge could cease just distal of the tapered opening 212. The membrane could be reflowed into place as a sleeve, or alternately a dip coating procedure could be used to form the cover. Similar to a reflowed cover, a dip coat could cease just distal of the tapered opening for ease of manufacture, thereby covering only the cylindrical section of the tubular section. In another example the entire proximal joint could be dip coated and the tapered opening trimmed from the resulting membrane. The properties of the membrane could be tuned by adjusting the controlled immersion factors of the dip coating process. For instance, where the membrane is not needed as part of a seal with the outer catheter, the cover can end distal of the tubular section 210 and does not stretch to the increased maximum radial size 224 of the tubular section.

In some examples the reinforcing polymer jacket 118 buttressing the proximal joint 100 in the locking zone 116 can extend the full length of the catheter guidewire 30. A longer jacket could further distribute the stiffness changes in the locking zone over a more substantial length. Similar to the cover 228 on the distal tubular section 210 of the catheter and catheter body 40, the jacket could also comprise a series of jackets having different moduli or thicknesses.

For some acute stroke conditions or embolic events, the therapy for retrieving an occlusion using aspiration alone is not possible. In situations where mechanical engagement of the occlusion is necessary, it can be desirable for the lumen 218 of the aspirating clot retrieval catheter to serve as a conduit for delivering a microcatheter and a thrombectomy clot retrieval device to a target occlusion. The clot retrieval device can be any of a number of commercially available products, many of which share similar common features. The expanded radial size 224 of the tubular section 210 of the proximal joint 100 still provides a seal with an outer catheter so that a suction source, such as a syringe or pump, can be applied to the outer catheter and transferred through to the tip of the clot retrieval catheter. The protective seal prevents the distal migration of any liberated clot debris from the thrombectomy procedure while also focusing the aspiration suction distally and restricting fluid proximal of the tip from being drawn into the catheter.

The invention is not limited to the examples described, which can be varied in construction and detail. The invention contemplates substitutions of component parts illustrated herein with other well-known and commercially available products. To those having ordinary skill in the art, these modifications are often apparent and are intended to be within the scope of the claims which follow.

The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician. Furthermore, the singular forms "a," "an," and "the" include plural referents unless the context clearly dictates otherwise.

In describing example embodiments, terminology is resorted to for the sake of clarity. It is intended that each term contemplates its broadest meaning as understood by those skilled in the art and includes all technical equivalents that operate in a similar manner to accomplish a similar purpose. The descriptions contained herein are examples of embodiments of the invention and are not intended in any way to limit the scope of the invention. While particular examples of the present invention are described, various modifications to devices and methods can be made without departing from the scope and spirit of the invention. Similarly, it is also to be understood that the mention of one or more components in a device or system does not preclude the presence of additional components or intervening components between those components expressly identified.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

The invention claimed is:

1. A proximal joint for linking a catheter body and a catheter guidewire, the proximal joint comprising:
   a distal end of the catheter guidewire, the distal end terminating at the proximal joint;
   a proximal end of a distal tubular section, the distal tubular section comprising:
   one or more axial spines,
   a tapered opening at the proximal end,
   an open distal end,
   a longitudinal axis, and
   a plurality of ribs defining a hollow internal lumen shared with the catheter body; and
   a proximal strut extending proximal to the distal tubular section from the one or more axial spines;
   wherein at least a portion of the proximal strut and a portion of the catheter guidewire are configured to overlap to form a locking zone;
   wherein the catheter body and distal tubular section are distal to the catheter guidewire, and
   wherein at least a portion of the distal tubular section is coated with a polymeric cover.

2. The proximal joint of claim 1, wherein at least a portion of the distal tubular section has a diameter larger than a diameter of the catheter body.

3. The proximal joint of claim 1, wherein the distal tubular section is formed integrally with the catheter body.

4. The proximal joint of claim 1, wherein the distal tubular section is cut from a hypotube.

5. The proximal joint of claim 1, wherein a perimeter of the tapered opening comprises one or more circumferential notches.

6. The proximal joint of claim 1, wherein one or more locking arms extend laterally from the proximal strut within the locking zone;
   wherein the one or more locking arms are configured to engage with one or more notches in the catheter guidewire within the locking zone.

7. The proximal joint of claim 1, wherein one or more locking pins extend radially from the catheter guidewire within the locking zone;
   wherein the one or more locking pins are configured to engage with one or more pockets in the proximal strut within the locking zone.

8. The proximal joint of claim 1, wherein at least a portion of the locking zone is covered by a reinforcing polymer jacket.

9. The proximal joint of claim 8, wherein a proximal end and a distal end of the reinforcing polymer jacket are tapered to be flush with surfaces of the proximal strut and catheter guidewire.

10. A proximal joint for connecting a catheter body and a catheter guidewire, the proximal joint comprising:
    a distal end of the catheter guidewire, the distal end terminating at the proximal joint;
    a proximal end of a tubular support structure, the tubular support structure having a proximal end and a distal end, the tubular support structure formed integrally with the catheter body and having a maximum radial size larger than a maximum radial size of the catheter body; and
    a proximal strut extending proximal to the tubular support structure and configured to mate with a distal portion of the catheter guidewire;
    wherein a reinforcing polymeric sleeve is disposed around a length of the proximal strut and a length of the catheter guidewire, wherein the catheter body and tubular support structure are distal to the catheter guidewire, and wherein the proximal end of the tubular support structure comprises a tapered opening, and the distal end comprises an open end.

11. The proximal joint of claim 10, wherein the tubular support structure comprises one or more axial spines and a plurality of loop ribs defining a hollow inner lumen shared with the catheter body.

12. The proximal joint of claim 11, wherein at least one of the one or more axial spines of the tubular support structure is aligned with the proximal strut.

13. The proximal joint of claim 10, wherein one or more locking arms extend laterally from the proximal strut, wherein the one or more locking arms are configured to engage with one or more notches in the catheter guidewire.

14. The proximal joint of claim 10, wherein a cover is disposed around at least a portion of the tubular support structure.

15. The proximal joint of claim 14, wherein the cover is adhered and/or stitched to the tubular support structure.

16. The proximal joint of claim 10, wherein at least a portion of the tubular support structure is coated with a lubricious low-friction coating.

17. A proximal joint for a clot retrieval catheter comprising a tubular section and a guidewire, the proximal joint comprising:
a distal end of the catheter guidewire, the distal end terminating at the proximal joint;
a proximal end of a distal tubular structure, the distal tubular structure comprising:
a tapered opening at a proximal end of the distal tubular section,
an open distal end,
one or more axial spines, and
a plurality of loop ribs defining a hollow inner lumen shared with the clot retrieval catheter,
the distal tubular structure extending proximally from the tubular section of the clot retrieval catheter; and
a proximal strut extending proximal to one of the one or more axial spines of the distal tubular structure and configured to form a mechanical lock with a distal portion of the catheter guidewire;
wherein a polymeric jacket bonds a length of the proximal strut and a length of the catheter guidewire, and
wherein the clot retrieval catheter and the distal tubular structure are distal to the catheter guidewire.

18. The proximal joint of claim 17, wherein at least a portion of the distal tubular structure is coated with a hydrogel.

19. The proximal joint of claim 17, wherein the tapered opening of the distal tubular structure contains one or more longitudinal slots.

20. The proximal joint of claim 17, wherein the distal tubular structure has a maximum radial size larger than a maximum radial size of the catheter body.

* * * * *